(12) United States Patent
Matuseski et al.

(10) Patent No.: US 6,378,377 B2
(45) Date of Patent: *Apr. 30, 2002

(54) ACOUSTIC REFLECTOR ATTACHMENT COMPATIBLE WITH NATIVE AIRCRAFT STRUCTURE

(75) Inventors: Timothy J. Matuseski, Inver Grove Heights; Derrick D. Hongerholt; Krishna M. Rajana, both of Eagan, all of MN (US)

(73) Assignee: Rosemount Aerospace Inc., Burnsville, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,294

(22) Filed: Apr. 23, 1999

(51) Int. Cl.⁷ .............................................. G01N 29/24
(52) U.S. Cl. .............................. 73/627; 73/600; 73/598; 73/629; 73/170.26; 340/582
(58) Field of Search .................... 73/597, 598, 600, 73/599, 629, 627, 170.21, 170.26; 340/580, 582

(56) References Cited

U.S. PATENT DOCUMENTS

| | | | | |
|---|---|---|---|---|
| 4,037,465 A | * | 7/1977 | Cook et al. | 73/623 |
| 4,412,315 A | * | 10/1983 | Flournoy | 73/623 |
| 4,461,178 A | | 7/1984 | Chamuel | 73/599 |
| 4,628,736 A | | 12/1986 | Kirby et al. | 73/590 |
| 4,833,660 A | | 5/1989 | Deom et al. | 367/157 |
| 5,095,754 A | * | 3/1992 | Hsu et al. | 73/602 |
| 5,357,228 A | | 10/1994 | Dufilie | 333/195 |
| 5,456,114 A | * | 10/1995 | Liu et al. | 73/597 |
| 5,629,485 A | | 5/1997 | Rose et al. | 73/599 |
| 5,729,508 A | | 3/1998 | Baker et al. | 367/176 |
| 5,922,958 A | * | 7/1999 | Schugt | 73/596 |

FOREIGN PATENT DOCUMENTS

EP    0 321 146    12/1988

* cited by examiner

Primary Examiner—Hezron Williams
Assistant Examiner—Nashmiya Fayyaz
(74) Attorney, Agent, or Firm—Westman, Champlin & Kelly, P.A.

(57) ABSTRACT

An ultrasonic ice detector that can be mounted directly to the skin of an aircraft includes a transducer that is coupled to the interior surface of the skin, and transmits acoustic vibrational energy through the skin. A reflector bar having a reflector surface is mounted on the interior surface of the skin at a location spaced from the transducer and is effective to reflect acoustic energy back to the transducer. The reflector bar is raised from the interior surface and preferably has a width equal to the width of the acoustic wave that is generated by the transducer at the reflector location. The transducer and reflector are non-intrusive and do not alter the aircraft skin structural integrity. The arrangement provides an accurate, responsive sensor for determining presence of ice or other contaminants on the exterior surface of the skin.

19 Claims, 3 Drawing Sheets

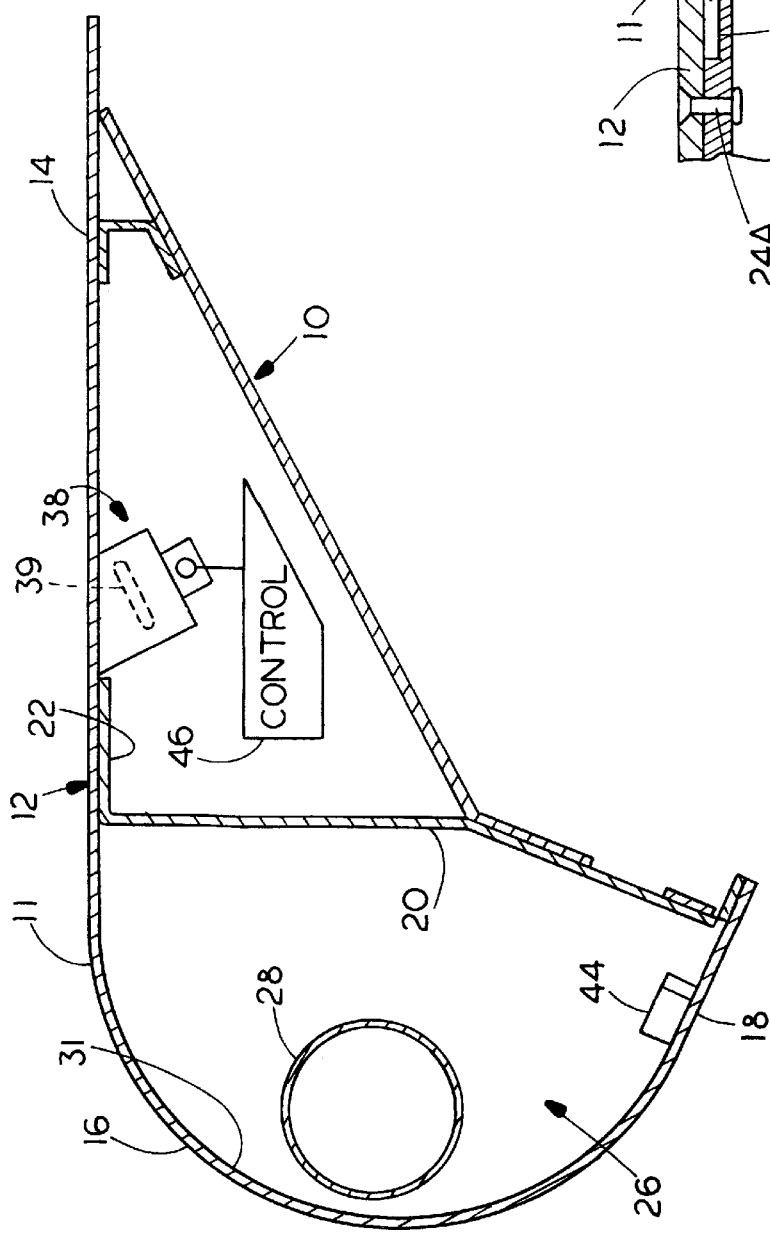
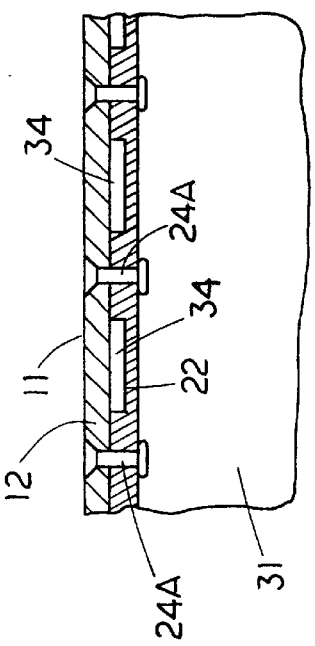

ACOUSTIC REFLECTOR ATTACHMENT COMPATIBLE WITH NATIVE AIRCRAFT STRUCTURE

CROSS REFERENCE TO RELATED APPLICATION

Reference is made to U.S. patent application Ser. No. 08/651,638, filed May 26, 1996 for ACOUSTIC CHANNEL FOR CONTAMINANT DETECTION now U.S. Pat. No. 5,922,958.

BACKGROUND OF THE INVENTION

The present invention relates to a wave transmitter/receiver and wave reflector which can be mounted directly to the interior surface of the skin of the aircraft, and does not depend upon the use of vibrating plates or other separate sensors that require modification of the aircraft surface.

The use of ultrasonic contaminant detectors is described in U.S. Pat. No. 5,629,485, where the orientation of transmitter and receivers onto a plate or sheet is taught, and a guided wave is transmitted through the sheet. The receiver receives a signal from the sheet and the presence of a contaminant on the sheet, such as ice, can be determined by the characteristics received of the wave or signal.

Additionally, U.S. Pat. No. 5,922,958 discloses a contaminant detection device that includes a plate that can be mounted onto the skin of an aircraft, and which includes a reflecting groove formed in the plate at a location spaced from a transducer/receiver.

U.S. Pat. No. 5,729,508 discloses an environmental seal for an acoustic transducer that can be used for transmitting ultrasonic vibrations in ice detecting systems such as the present invention.

U.S. Pat. No. 4,461,178 also discusses contaminant detection using guided waves.

SUMMARY OF THE INVENTION

The present invention relates to an ultrasonic ice detection system which can be mounted directly onto interior surfaces of an aircraft skin or outer wall, or on a component of an airborne vehicle, such as the inlet of a turbine engine, or on other structures, without having a separate sheet or plate installed. The sensor is non-intrusive in the form disclosed. The invention uses a transmitter/receiver oriented to transmit vibrations at a particular phase velocity. The vibration will propagate through the aircraft skin or wall, and a reflector bar is located at a predetermined position to provide an adequate reflected wave. The reflector location is selected to optimize performance.

Both the transducer assembly and the reflector bar are secured to the interior surface of the skin of an aircraft, so that the sensor components mount interiorly of the aircraft. There is no need for providing a separate waveguide plate that requires alteration of the aircraft structure or the aircraft skin. There is also no need to cut reflective surfaces on the aircraft or engine housing wall itself. Providing an acoustic energy path along the skin or wall that is free of rivets or other attached structures insures propagation and the ability to detect changes in vibrational frequency and/or amplitude due to contaminants, such as ice, bonding to exterior surfaces of the aircraft skin.

In one aspect of the invention, as shown, the moveable slat at the leading edge of the wing, which is used for changing lift characteristics of the wing, is illustrated as an exemplary form of the invention. The exemplary form shows that the acoustic energy can be transmitted along curved wall structures to the reflector bar, and as well as being capable of reflecting acoustic energy along flat plates.

Parameters for determining the height and depth of the reflector can be optimized by experimental procedures, or by finite element analysis or boundary element analysis utilizing numerical methods.

BRIEF DESCRIPTION OF THE DRAWINGS

FIG. 2 is a side view of the leading edge slat shown in FIG. 1;

FIG. 3 is a sectional view illustrating an air duct passage that provides for a rivet free path for acoustic energy from the transducer of the present invention;

DETAILED DESCRIPTION OF THE PREFERRED EMBODIMENTS

Figure 1:
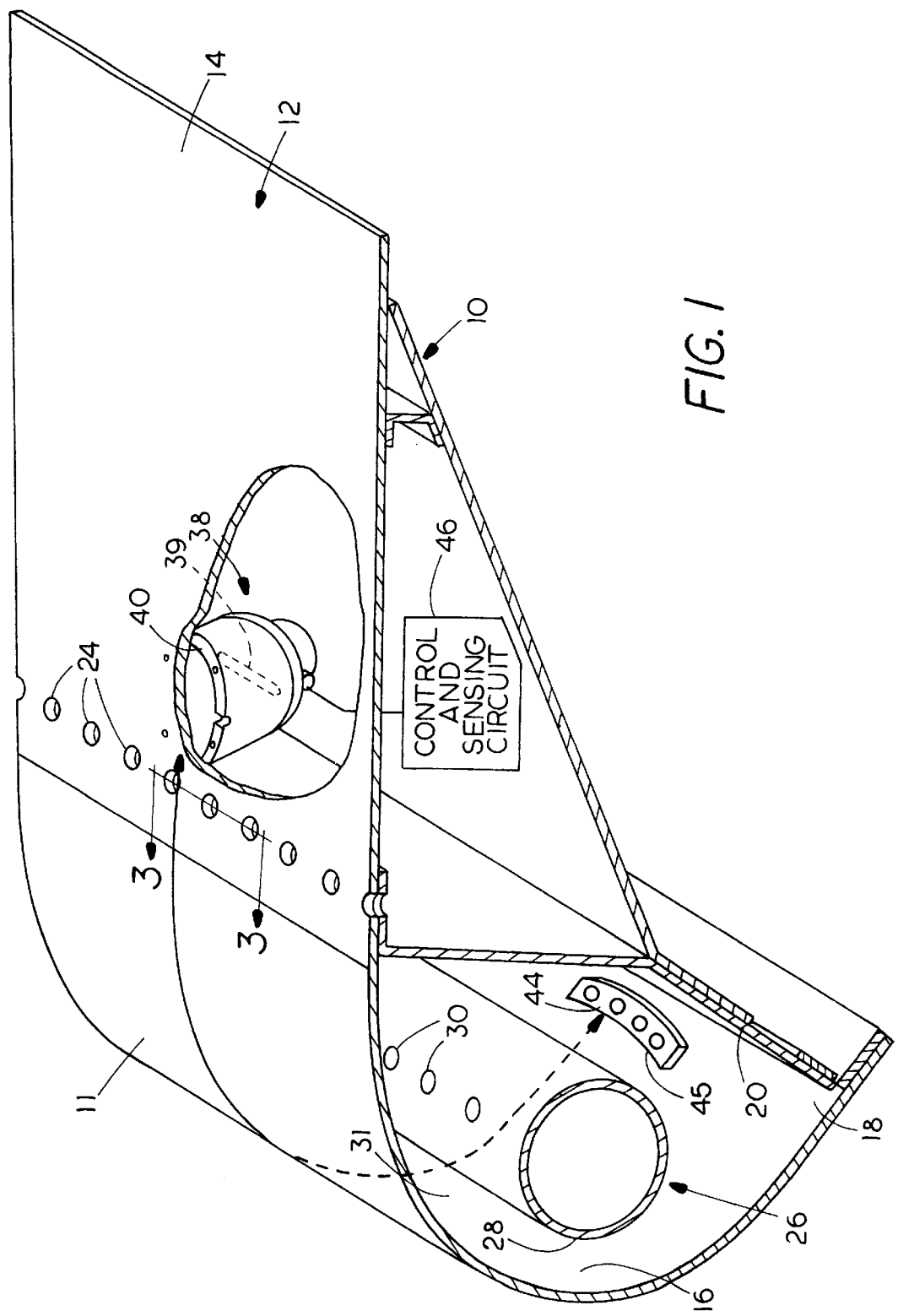
FIG. 1 is a perspective view of a portion of a typical leading edge slat of a wing of an aircraft having a detection system made according to the present invention installed thereon.

Referring to FIG. 1, a leading edge slat assembly 10, for an airfoil or wing, comprises an aircraft structure that has an exterior skin or wall 12, manufactured, in this instance, to include a planar top plate section 14, and a curved airfoil leading section 16 that has a trailing end flat portion 18 extending rearwardly from the leading edge. The planar portion 18 is reinforced with a bulk head 20 that is made to extend up to the plate section 14, and it has a bent leg section 22 that is riveted to the plate section 14 with suitable flush rivets in openings 24. The curved airfoil section 16 portion defines an interior chamber 26 which has a concave interior surface 31, in which a hot air duct 28 used for deicing purposes is provided. This duct 28 is called a "piccolo" tube because it will have a number of openings in desired locations, such as those indicated at 30, that will permit hot air to flow along the interior surface 31 of the chamber 26, and through recesses in the junction of the outer skin section 14 and the bent leg section 22 that form hot air ducts 34 shown in FIG. 3. The ducts 34 shown in FIG. 3 are greatly enlarged. The rivets 24A in opening 24 are illustrated and the ducts 34 are between the rivets. The air ducts provide a channel for directing acoustic energy that is free of vibration reflecting structures, such as rivets.

An ultrasonic or acoustic energy transducer assembly comprising a transmitter/receiver 39 and a mounting housing indicated generally at 38 has an end surface 40 bonded and secured intimately with the under surface of the flat plate section 14, adjacent to the bent lip 22, and in a position so that the acoustic energy transmitted or generated by a piezoelectric or other suitable ultrasonic transmitter/receiver 39 in the transducer assembly 38 will be propagated through one or more of the ducts 34 and across and along the concave wall section 16. Magnetostrictive elements and electromagnetic acoustic transducers can be used as well.

An acoustic energy reflector discontinuity comprising a bar 44 is securely and intimately adhered to the interior surface 31 adjacent or on the flat portion 18 of the aircraft skin or wall at a selected location in the path of propagation of ultrasonic vibration from the transducer assembly 38. The reflector bar 44 has a curved reflector surface 45. The surface 45 is perpendicular to the interior surface 31. The height of bar 44 is shown schematically at 60 in FIG. 4, and also shown with a depth 62 that is parallel to the direction of wave propagation. The width 66 of energy discontinuity reflector bar 44 measured perpendicular to the direction of wave propagation also is selected to provide optimum reflection and sensitivity to contaminants on the exterior surface 11 of the aircraft skin 12.

The transducer assembly 38 is connected to a computer based control and sensing circuit 46 which is on board the aircraft. The control computer is programmed to excite the transducer 39 to launch acoustic energy or vibration that is transmitted through the skin 12, and to alternately receive signals from the transducer 39 when it is vibrated from returning or reflected energy in the same manner as those explained in U.S. Pat. No. 5,922,958, and using a transducer that is assembled and oriented similarly to that shown in U.S. Pat. Nos. 5,729,508 and 5,629,485.

Thus, the transducer is controlled to transmit a pulse or burst of acoustic energy and then be still for a time to receive a reflected vibration. The presence of contaminants on the surface can be determined by examining the characteristics of the signal reflected and received at the transducer relative to the transmitted signal.

Again, it can be seen in FIGS. 1 and 2 that the transducer assembly 38 and the acoustic energy reflector discontinuity 44 are on the interior surfaces of the skin or wall to be sensed. The transducer and the reflector are both bonded in place with suitable adhesives, or can be riveted or otherwise fastened in place. Flush head rivets are used so that no protrusions into the air stream exist, and no notches or other fitting modifications have to be made to the exterior of the aircraft skin.

Figure 4:
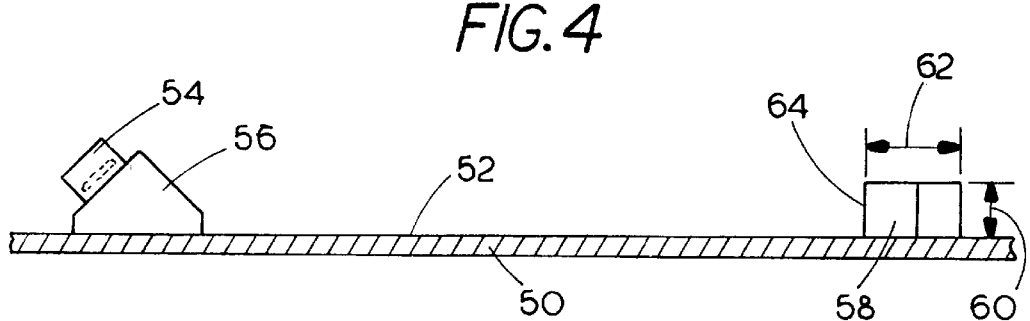
FIG. 4 is a schematic representation of the transducer and reflector assembled on the internal surface of aircraft skin.
Figure 5:
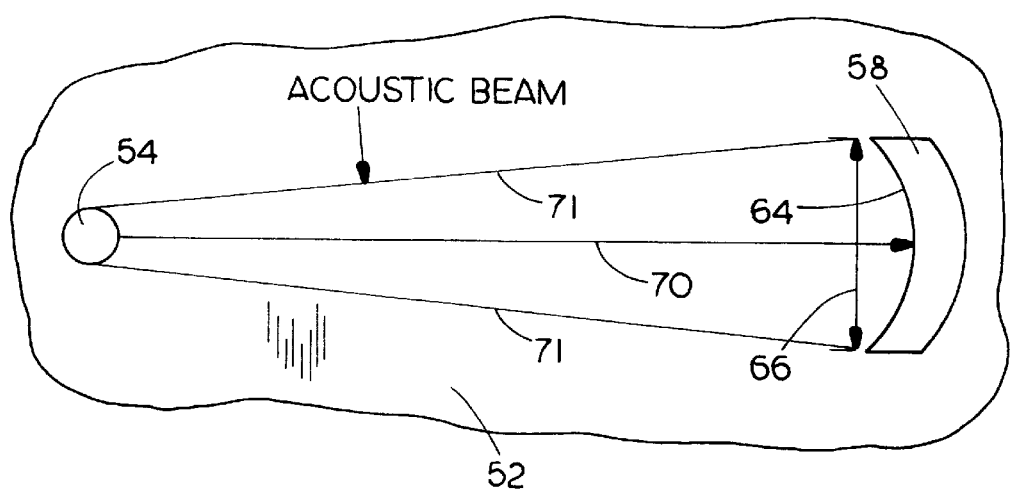
FIG. 5 is a schematic representation of the propagation path of acoustic energy from the transducer of FIG. 4.

FIGS. 4 and 5 are schematic representations of the aircraft skin illustrated generally at 50 having an interior surface 52 on which a transducer assembly 54 is mounted, and illustrate the principals of the present invention. The wall or skin 50 may be an aircraft body, turbine engine inlet, a separate structure such as a high tower or a bridge, or any other structure exposed to icing conditions. The primary use envisioned is for airborne vehicles.

The transducer assembly 54 is a transmitter and receiver and is mounted on a wedge 56 that transmits the energy at a selected angle relative to the interior surface 52 of the skin 50 and obtain a desirable efficiency of operation. The transducer assembly 54 is also mounted at a suitable angle relative to the plane of the skin, as shown. An acoustic energy reflector discontinuity, comprising a bar 58, is mounted at a distance spaced from the transducer 54 and will reflect acoustic energy back to the transducer receiver section to receive the reflected vibrations and provide the signals to the computer control 46 for analysis. The height and depth of the reflector bar 58 are represented at 60 and 62, and depending on factors such as the frequency of transmission and the like, these dimensions may be selected by experimental procedures, or the dimensions can be developed using numerical methods such as finite element analysis or boundary element analysis to determine the proper size relationship of the bar for optimum performance. The cross section profile of the reflector 58 can vary depending on the wave type and/or mode. While a rectangular cross section is shown, other examples could be triangular, rhombus, square or semi-cylindrical.

FIG. 5 illustrates the width of the reflector 58, and it also shows that the surface 64 which faces the transducer 54 is curved into an arc centered on the transducer, across the width of the reflector 58. The width is represented by the double arrow 66. In FIGS. 1 and 2, the curved edge surface is indicated at 45, and faces the transducer 38. The reflecting surface 64 extends outwardly from the interior surface of the wall or skin. The transducer 54 shown schematically in FIG. 5 is intimately bonded to the interior surface 52 of the wall or skin, and the reflector bar 58 is bonded securely as well. The reflector can be an integral surface discontinuity such as a rib or groove formed from or formed into the wall material. The curve of the surface 64 is non planar and can be concave as shown, or some other arbitrary shape that functions to reflect and focus acoustic energy towards the receiver.

The distance from the transducer 54 to the reflector bar 58 is represented by the arrow 70, and in the case of a concave reflector surface 64 as shown in FIG. 5, forms the radius of curvature of the reflecting surface 64 for increasing efficiency by providing a focusing effect of the reflected wave. The wave path of the acoustic beam of vibrational energy is indicated by the lines 71.

The width of the reflector bar represented by the double arrow 66 is selected for maximum efficiency, so that the width substantially equals the acoustic beam width at the position where the acoustic wave front and the reflector bar meet. For a bulk wave, this width can be given as a function of transducer geometry and frequency. For a circular transducer, the equation for guided waves is given in Rayleigh and Lamb waves, Physical Theory and Applications, I. A. Viktorov, Plenum Press, New York, 1967.

Thus, by orienting the reflector at a selected distance from the transducer, and insuring that the generated acoustic energy is not reflected from rivets or other random discontinuities in the wall or skin, a sensitive detector for detecting contaminants on the exterior surface of the wall or skin of an aircraft or other structure is provided. Rivets tend to scatter energy and random discontinuities will not provide optimum performance that can be achieved with a properly designed and positioned reflector.

The attachment method for the reflector to the interior surface of the wall or skin should address two criteria. First, the attachment method should provide acoustic coupling that is adequate between the reflector and the wall or skin. This can be accomplished by traditional liquid couplants, dry couplants, or adhesive couplants. The couplant thickness should be thin enough to reduce acoustic losses across the interface between the surface of the skin and the transducer. Secondly, the attachment method must provide the required mechanical stability. Rivets and/or external clamping can be used to hold the reflector and the couplants in place. The reflector will reflect the acoustic energy wave back to the transducer, where the transmitter/receiver element detects changes in the reflected wave from the transmitted wave, and this provides an indication of changes in the surface conditions on the exterior of the skin.

The transducer and reflector mount on the interior of the aircraft structure and are thus non-intrusive and do not affect airflow across the aircraft exterior. Use of the invention results in no reduction in aerodynamic efficiency or aircraft performance. In an example, an acoustic path between the reflector and the transducer is approximately 12 inches on a wing leading edge slat. The reflector material is preferably selected to match that of the aircraft skin, so expansion and contraction characteristics are the same and the acoustic coupling of the reflector is excellent. The reflector surface in contact with the skin is machined to match the contours of the airfoil or other structure at the location where it is installed. If mounted on a curved concave or convex surface, the reflector surface will be curved. This will reduce the bond layer thickness between the reflector and the aircraft skin so that the bonding is not a substantial deterrent to transmission of ultrasonic energy. The acoustic bond between the reflector and the skin is preferably made with high strength adhesive capable of withstanding extreme temperatures and well known in the art. The selected adhesive should also match well with the temperature environment. As stated, rivets can also be used, as can press fit nuts that are assembled into attachment holes with screws, to hold a reflector in place along with the adhesive. If fasteners are used, they must be of the flush mounted type in order to avoid disturbance of the airflow over the exterior aircraft structure.

The transducer 38 has a mounting wedge so the piezoelectric element is positioned at a desired angle. Pairing of frequency and phase velocity of the acoustic wave makes it possible to differentiate between types of particles, such as water and ice on the surface and makes optimization of contaminant detection a reality. By selecting the appropriate frequency range of transmission of acoustic energy, which can be determined analytically by knowing the configuration of the skin or wall, a "Lamb" wave can be generated in the skin. The acoustic wave will resonate and will be reflected back by the reflector bar. The frequency of the acoustic vibration is selected to match the geometry of the mounting locations on the aircraft skin. Frequencies in the range of 0.5 MHz to 3 MHz are satisfactory for the application disclosed. By selecting frequency of operation, different densities of contaminants can be detected. The single transducer illustrated can be used for both transmitting and receiving acoustic vibrations, for example by having intermittent operation controlled by the computer based controls 46 so that a transmission would occur in a burst and the transducer would then be a receiver to receive reflected waves to provide an output. A separate transmitter and separate receiver also can be used to form the transducer assembly. The transmitter and receiver will be adjacent and together form a transducer assembly.

Piezoelectric sensor elements are capable of transmitting energy or vibration at selected frequencies when energized with an external signal, controlled by computer based controls 46, and can generate an electric signal from reflected vibrations that are received. The techniques of transmitting and receiving acoustic vibrations are well known, and include other vibration generators, as stated.

Although the present invention has been described with reference to preferred embodiments, workers skilled in the art will recognize that changes may be made in form and detail without departing from the spirit and scope of the invention.

What is claimed is:

1. A contaminant detection sensor for a wall with an exterior surface and an interior surface, the exterior surface being subjected to airflow in use, the detection sensor comprising a transmitter and receiver coupled to the interior surface of the wall at a first location and providing an acoustic energy pulse forming an acoustic wave transmitted along the wall, and a reflector discontinuity comprising a vibration reflector bonded on the interior surface of the wall at a position spaced from the transmitter, the vibration reflector comprising a bar extending outwardly from the interior surface and operable to reflect the acoustic wave transmitted from the transmitter through the wall and back to the receiver through the wall, and the reflected acoustic wave changing in characteristics when contaminants are present on the wall between the first location and the reflector bar.

2. The sensor of claim 1, wherein the receiver receives the reflected acoustic wave and provides an output-that is a function of the state of the exterior surface.

3. The sensor of claim 1, wherein the reflector has a curved surface extending outwardly from the interior surface and facing the transmitter and receiver.

4. The sensor of claim 3, wherein said curved surface has a radius substantially equal to the distance from the transmitter to the curved surface.

5. The sensor of claim 1, wherein said reflector discontinuity is constructed of the same material as the wall.

6. The sensor of claim 1, wherein the reflector bar has a width measured perpendicular to a center line between the transmitter and the reflector bar, the width being substantially equal to the width at the location of the reflector bar of an acoustic wave transmitted by the transmitter.

7. The sensor of claim 1, wherein said wall comprises a curved edge portion of an air foil shape, and the transmitter and reflector discontinuity are spaced apart along a concave portion of the wall.

8. The sensor of claim 1, wherein said reflector bar is coupled to the interior surface with a high temperature and high strength adhesive.

9. The sensor of claim 1, wherein a surface of a reflector engaging the interior surface of the wall is conformed to the shape of the interior surface of the wall, and wherein the interior surface has a non planar cross section.

10. A contaminant detection system for a structure having a wall with an exterior surface and an interior surface, the exterior surface being subjected to airflow and subject to having contaminants deposited thereon, the detection system comprising a transmitter and receiver coupled to the interior surface of the wall of the structure at a first location, the transmitter transmitting acoustic energy causing vibrations in the wall of the structure propagated along a vibration wave path in the wall of the structure, and a reflector discontinuity member mounted on and protruding from the interior surface of the wall of the structure at a position spaced from the transmitter and receiver and in the vibration wave path to reflect acoustic energy back to the receiver through the wall of the structure, the reflected acoustic energy being affected by presence of contaminants on the exterior surface of the wall of the structure.

11. The system of claim 10 wherein the reflector discontinuity member has a curved surface extending outwardly from the interior surface and facing the transmitter and receiver.

12. The system of claim 11, wherein the reflector discontinuity member comprises a bar attached to the interior surface and having a width measured perpendicular to a center line between the transmitter and the reflector bar, the width being substantially equal to the width of the vibration wave path at the location of the reflector bar.

13. A method of sensing contaminants adhering to an exterior surface of a wall of a structure over which air flows, comprising mounting an acoustic transducer on an interior surface of the wall, mounting a reflector bar directly on the interior surface of the wall at a location spaced from the transducer, transmitting vibrational energy along the interior surface of the wall in a path toward the reflector, and sensing vibrational energy reflected from the reflector along the interior surface.

14. The method of claim 13 including sensing the reflected energy at the transducer.

15. The method of claim 14 including forming a surface of the reflector to focus reflected vibrational energy at the transducer.

16. The method of claim 13, wherein the wall is the skin of an aircraft.

17. An apparatus for detecting the presence of contaminants along an exterior surface of a curved leading edge of an aircraft wing, the wing having an interior surface opposed to the exterior surface, comprising a transducer acoustically coupled directly to the wing interior surface at a location downstream of the wing leading edge, and including a transmitter for sending an acoustic wave along a wave path that extends in a direction upstream from said transducer, and around the curved leading edge, a reflector bar protruding from acoustically coupled to the wing interior surface, said reflector bar having a reflecting surface that extends outwardly from the interior surface of the aircraft wing for reflecting the acoustical wave sent from the transmitter back to the transducer, the reflected acoustical wave being affected by contaminants on the exterior surface.

18. The apparatus of claim 17, wherein the reflector is of the same material as the aircraft wing.

19. The apparatus of claim 17, wherein said reflector bar extending above the interior surface is nonplanar transversely to the wave path.

* * * * *

UNITED STATES PATENT AND TRADEMARK OFFICE
CERTIFICATE OF CORRECTION

PATENT NO.     : 6,378,377 B2
DATED          : April 30, 2002
INVENTOR(S)    : Timothy J. Matuseski et al.

It is certified that error appears in the above-identified patent and that said Letters Patent is hereby corrected as shown below:

Column 6,
Line 62, after "surface" insert -- as a measure of contaminants on the wall of the structure. --.

Column 7,
Line 12, after "from" insert -- and --.

Signed and Sealed this

Twenty-sixth Day of November, 2002

Attest:

Attesting Officer

JAMES E. ROGAN
Director of the United States Patent and Trademark Office